(12) United States Patent
Crowder

(10) Patent No.: US 8,789,962 B2
(45) Date of Patent: Jul. 29, 2014

(54) SURGICAL HEADLIGHT

(75) Inventor: Austin Crowder, Dallas, TX (US)

(73) Assignee: Vikon Surgical, LLC, Birmingham, AL (US)

( * ) Notice: Subject to any disclaimer, the term of this patent is extended or adjusted under 35 U.S.C. 154(b) by 565 days.

(21) Appl. No.: 11/259,978

(22) Filed: Oct. 27, 2005

(65) Prior Publication Data
US 2007/0097702 A1   May 3, 2007

(51) Int. Cl.
*F21V 21/084*  (2006.01)
*A61B 5/00*  (2006.01)
*F21Y 113/00*  (2006.01)
*A61B 19/00*  (2006.01)
*F21Y 101/02*  (2006.01)

(52) U.S. Cl.
CPC ......... *F21V 21/084* (2013.01); *F21Y 2113/005* (2013.01); *A61B 19/5202* (2013.01); *G02B 6/0006* (2013.01); *A61B 19/52* (2013.01); *A61B 5/6814* (2013.01); *F21Y 2101/02* (2013.01); *A61B 2019/262* (2013.01); *Y10S 362/804* (2013.01)
USPC ............ 362/105; 362/572; 362/570; 362/804

(58) Field of Classification Search
USPC ......... 362/572, 551, 552, 554, 555, 570, 573, 362/574, 105, 221, 804; 351/158
See application file for complete search history.

(56) References Cited

U.S. PATENT DOCUMENTS

| | | | | |
|---|---|---|---|---|
| 3,285,242 A | * | 11/1966 | Wallace | 600/249 |
| 3,645,254 A | * | 2/1972 | Burton | 600/249 |
| 3,745,993 A | * | 7/1973 | Feinbloom | 600/249 |
| 3,830,230 A | * | 8/1974 | Chester | 600/249 |
| 3,951,139 A | * | 4/1976 | Kloots | 600/249 |
| 4,616,257 A | * | 10/1986 | Kloots et al. | 348/370 |
| 5,774,271 A | * | 6/1998 | Lagerway et al. | 359/649 |
| 5,867,320 A | * | 2/1999 | Park et al. | 359/618 |
| 6,113,281 A | | 9/2000 | Davis | |
| 6,224,227 B1 | * | 5/2001 | Klootz | 362/105 |
| 6,231,193 B1 | | 5/2001 | Sugawara | |
| 6,639,733 B2 | | 10/2003 | Minano | |
| 6,896,381 B2 | | 5/2005 | Benitez | |
| 6,896,389 B1 | * | 5/2005 | Paul | 362/105 |

(Continued)

FOREIGN PATENT DOCUMENTS

WO     WO 02099332 A1 *  12/2002

OTHER PUBLICATIONS

Enova: Halo Cordless Surgical Headlight; http://www.enovamedical.com/; total page count 16.

(Continued)

*Primary Examiner* — Robert May
(74) *Attorney, Agent, or Firm* — C. Brandon Browning; Maynard Cooper & Gale, PC

(57) ABSTRACT

A surgical headlight that uses multiple LEDs to produce superior illumination. Heat sinks are used to help dissipate heat produced from the LEDs. The light from the LEDs is directed, using collimizers, into fiber optic cables. The fiber light from the optic cables, using an LED combiner, is then combined and focused on a working area. The LED combiner may include an adjustable lens so that the device's illumination may be focused at multiple focal distances and with varied areas of illumination. The LEDs may be powered by a battery and may comprise one or more red LEDs, one or more blue LEDs, and one or more green LEDs.

30 Claims, 3 Drawing Sheets

(56) References Cited

U.S. PATENT DOCUMENTS

| | | |
|---|---|---|
| 6,908,208 B1 * | 6/2005 | Hyde et al. ............... 362/105 |
| 6,986,591 B2 | 1/2006 | Pate |
| 7,153,015 B2 | 12/2006 | Brukilacchio |
| 7,181,378 B2 | 2/2007 | Benitez |
| 7,229,202 B2 * | 6/2007 | Sander ..................... 362/575 |
| 2003/0042493 A1 * | 3/2003 | Kazakevich ............... 257/98 |
| 2004/0149998 A1 * | 8/2004 | Henson et al. ............. 257/98 |
| 2004/0151008 A1 * | 8/2004 | Artsyukhovich et al. ..... 362/572 |
| 2004/0246744 A1 * | 12/2004 | Krupa et al. ............... 362/574 |
| 2005/0243570 A1 | 11/2005 | Chaves |
| 2006/0133069 A1 | 6/2006 | Clupper |

OTHER PUBLICATIONS

Welch Allyn: Product Search; http://www.welchallyn.com/; total page count 6.

\* cited by examiner she# SURGICAL HEADLIGHT

BACKGROUND OF THE INVENTION

1. Field of the Invention

The present invention relates to apparatuses and methods for illuminating work areas such as surgical fields.

2. Description of the Related Art

Medical providers use surgical headlights to illuminate a surgical field. Such headlights are worn on the medical provider's head and may utilize halogen or metal halide light sources, as well as xenon lights, to provide illumination. The Xenon light source may be located on a rack. The light source projects light, via a fiber optic cable, to the headlight system. Light emitting diodes (LEDs) may also be used, providing various advantages over prior illumination methods including reducing the weight, cost, heat, maintenance and discomfort generally associated with the traditional headlight. Drawbacks for these devices include: limited bulb life, excessive cost, fragile fiber optic cables, insufficient illumination, and limited mobility for the user.

Examples of related devices include the 49820 Xenon Surgical Headlight System from WelchAllyn [WelchAllyn, Inc., 4341 State Street Road, Skaneateles Falls, N.Y. 13153-0220 USA]. The device connects a Xenon light source, instead of LEDs, to a headlamp using fiber optic cables. The device is attached to a light source that has limited to no mobility. This constrains the user who is tethered, via the fiber optic cables, to the light source. Unsurprisingly, the fiber optic connection between the lamp and light source is placed under great strain, resulting in reliability issues for the headlight unit. WelchAllyn also supplies the 49020 5 watt LED Procedure Headlight, which utilizes a single 5 watt LED and produces 100 Lumens of white light. In addition, the HALO headlight, by Enova Medical Technologies [1839 Buerkle Road, St. Paul, Minn. 55110 USA], uses two white LEDs and no fiber optic cables. However, the prior art's limited use of LEDs results in brightness that is not optimal, thereby producing less light than more traditional surgical headlights such as Xenon-board devices.

Thus, a need exists for a mobile surgical headlight that utilizes LEDs to lower cost, weight and heat, while still providing light adequate to illuminate the working area.

SUMMARY OF THE INVENTION

In one embodiment of the invention, a surgical headlight comprises multiple LEDs. Each LED is powered by a battery. Each LED is coupled to a heat sink to promote heat dissipation. Furthermore, each LED is connected to a collimator that directs light from the LED into a fiber optic cable. The collimator may comprise or be coupled to one or more lenses. The fiber optic cables guide light from the LED towards a LED combiner. There, the light from each LED is directed so that each LED's light is combined with light from the other LEDs. The surgical headlight produces light of an intensity greater than about 100 lumens. In other embodiments of the invention, the headlight produces light of an intensity greater than about 300 lumens. Still other embodiments produce light greater than about 500 lumens.

In another embodiment of the invention, the headlight comprises three LEDs while in other embodiments, the headlight comprises six, nine or twelve LEDs. In one embodiment of the invention, a blue LED, a red LED and a green LED combine to produce white light. In another embodiment, a filter is used to remove color components from one or more LEDs. In still another embodiment, current balancing circuitry is used to vary the intensity of one or more of the multiple LEDs.

In yet another embodiment of the invention, the LED combiner comprises a lens and an actuator for actuating the lens. As a result, the light from the LEDs may be focused at various focal points.

In still another embodiment of the invention, the collimator comprises a dowel.

In another embodiment of the invention, the LEDs are mounted on a headlight. In other embodiments, the LEDs are mounted on a belt worn around the user's waist or on a belt fastened to the user's arm. The battery or batteries, that supply energy to LEDs, may be mounted on the headlight or on a belt worn around the user's waist or arm.

One embodiment of the invention weighs less than about 12 ounces.

In still another embodiment, the invention is used to illuminate a surgical scope or, for example, a retractor involved in endoscopic procedures.

The foregoing has outlined rather broadly the features of the present invention in order that the detailed description of the invention that follows may be better understood. Additional features and advantages of the invention will be described hereinafter, which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which.

DESCRIPTION OF THE PREFERRED EMBODIMENT(S)

Figure 1:
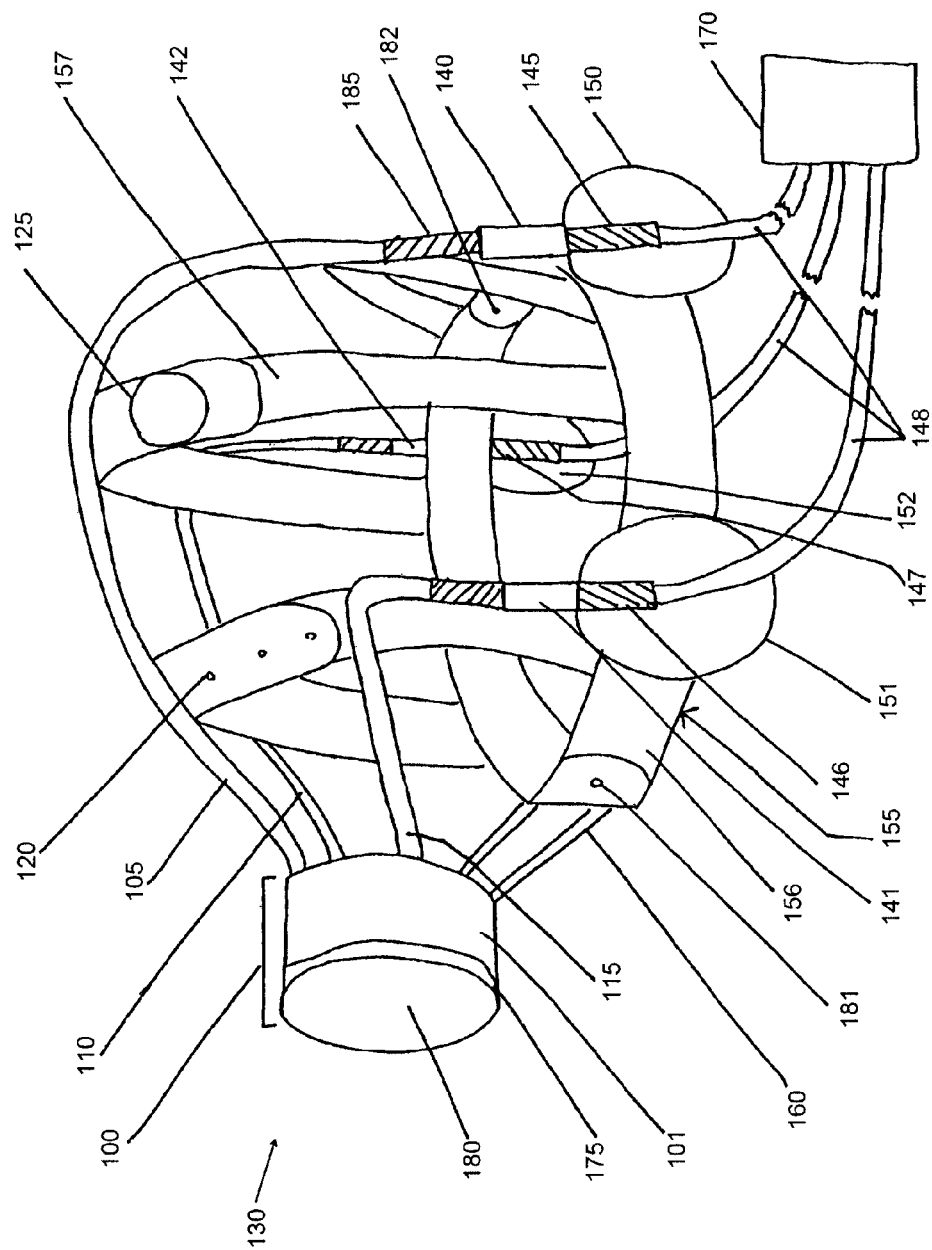
FIG. 1 is an example of one embodiment of a surgical headlamp.

FIG. 1 illustrates one embodiment of the invention. A surgical headlight 130 comprises three LEDs 145, 146, 147. Each LED 145, 146, 147 is powered by a battery 170. Each LED 145, 146, 147 may be powered by its own power supply (e.g., battery 170) or one power supply may power all of the LEDs 145, 146, 147. The LEDs 145, 146, 147 may connect to the battery 170 (e.g., lithium-ion) via electrically shielded cables 148 or, for example, an integrated circuit or BUS. The battery may be located on a headlight 130 or on a belt fastened to the user's arm or waist. In one embodiment of the invention, the battery 170 is capable of producing 10 volts per every 5 watt LED and could last 4 or more hours between recharging sessions. The battery 170 may be capable of "hot swapping" whereby a charge is retained thereby allowing the headlamp 130 to temporarily produce light while batteries 170 are exchanged.

Each LED 145, 146, 147 may be coupled to a heat sink 150, 151, 152 to promote heat dissipation. Each LED may be coupled to its own individual heat sink 150 or multiple LEDs 145, 146, 147 may utilize one such heat sink. In addition, fans may be used to cool the LEDs 145, 146, 147 and/or heatsink 150. Heat sinks 150, 151, 152 because high powered LEDs 145, 146, 147 produce heat that must be dissipated to avoid causing the user discomfort. Due to the amount of heat generated by the LEDs 145, 146, 147, the heat sinks 150, 151, 152 may be distanced from the user by one to two inches. Such a position not only allows the user to be located a reasonable distance from the heat source, but also allows for airflow around the LED to promote cooling. The heat sinks 150, 151, 152 may have a "waffle" or "honeycomb" shape to increase their surface area and thus enable faster dissipation of heat. The heat sinks may be made of any low weight, conductive material such as, for example, airplane aluminum, polycarbonate/metal alloys, fiber glass or bubble glass.

The LEDs 145, 146, 147 selected may, for example, comprise the 5 watt Luxeon III Star and/or Luxeon V Star, available from Lumileds Lighting, LLC (370 West Trimble Road, San Jose, Calif., 95131 USA). Those of ordinary skill in the art will appreciate that other LEDs may be used. Lower wattage LEDs (e.g., 1 or 3 watts) may also be used if less heat and brightness are acceptable design choices. The LEDs may be selected according to the desired end use for the headlamp 130. For example, in neurological surgery, tissue differentiation is critical and thus, white light, of extreme brightness, is advantageous. Furthermore, "cool" lighting is desirable in order to avoid drying tissues during a procedure. To that end, color temperature of 5,000 degrees Kelvin, or less, may be advantageous.

To achieve a high level of bright white light (e.g., 500 lumens) with LEDs, blue LEDs may be filtered, thus leaving white light. In addition, such light may be generated by using a combination of lights such as, for example, red, blue, and green lights. In one embodiment of the invention, as seen in FIG. 1, the headlight 130 comprises three LEDs 145, 146, 147 comprising one red 145, one green 146 and one blue 147 LED. To increase brightness, other embodiments of the invention may comprise six, nine or twelve LEDs. For example, one embodiment of the headlight 130 may comprise four red LEDs, four green LEDs and four blue LEDs. According to design preference, a red LED 145 may, for example, be replaced or coupled with a red-orange or amber LED. A blue LED 147 may be replaced or coupled with royal blue LEDs. Choosing different colors, and possibly adjusting current delivered to such LEDs, allows the headlight 130 to achieve varied levels of brightness in exchange for, as an example, varied levels of power consumption. Such flexibility also allows for cost, performance, and availability variances associated with differently colored LEDs to be accounted for without substantially varying the operation principles of the headlight 130.

In one embodiment, color LEDs may be coated with a phosphorus coating to create white light from, for example, a blue LED 147. As those of ordinary skill in the art will appreciate, color LEDs or LEDs with varied coatings may be incorporated into the headlight 130 to compensate for light color that is missing from the headlight 130 light spectrum.

To vary the intensity of light produced from each LED 145, 146, 147, a person of ordinary skill in the art will appreciate how current balancing circuitry may be used to distribute current in varying levels to different LEDs. Accordingly, less current may be supplied to, for example, the red LED 145 than the blue LED 147. Adjusting the current level allows the headlamp 130 to produce white light with no color tint. However, high current levels may be supplied to, for example, the red LED 145 to produce light with a red tint. Different medical users may choose different tints to illuminate varied tissues such as, blood vessels, bone or connective tissue. As appreciated by those of skill in the art, various techniques for dimming light from all or any LED 145, 146, 147 may be used. Typical techniques include pulse width modulation or current amplitude dimming with, for example, potentiometers and related circuitry. In one embodiment, an Ostar, available from Osram Semiconductors (Gmbh Wernerwerkstrasse 2 D-93049, Regensburg, Germany) (www.osram-os.com), may be used to adjust illumination from different colored LEDs to produce white light.

Referring to FIG. 1, the LEDs 145, 146, 147 may be coupled to an LED driver to regulate current to the LEDs. An example of such a driver is the 12VDC 5 W LED Drive Module PowerPuck (Model #2008) from LED dynamics. (LuxDrive, Division of LEDdynamics, Inc., 44 Hull Street, Randolph, Vt. 05060-0444). Such a DC to DC converter delivers a fixed output current by varying the output voltage as required to maintain the specified current. The drivers may be calibrated so that different levels of current are supplied to different LEDs to ensure white light is produced. Such current levels may be fixed or variable, as appreciated by those of ordinary skill in the art.

Through use of multiple LEDs, the surgical headlight 130 may produce light of an intensity greater than about 300 lumens. Blue LEDs are typically capable of 23 lumens, red LEDs may produce 140 lumens and green LEDs may produce 64 lumens. When white light of insufficient brightness is produced, the number of LEDs can be increased. Using, for example, twelve LEDs may produce light of an intensity greater than about 500 lumens.

Figure 2:
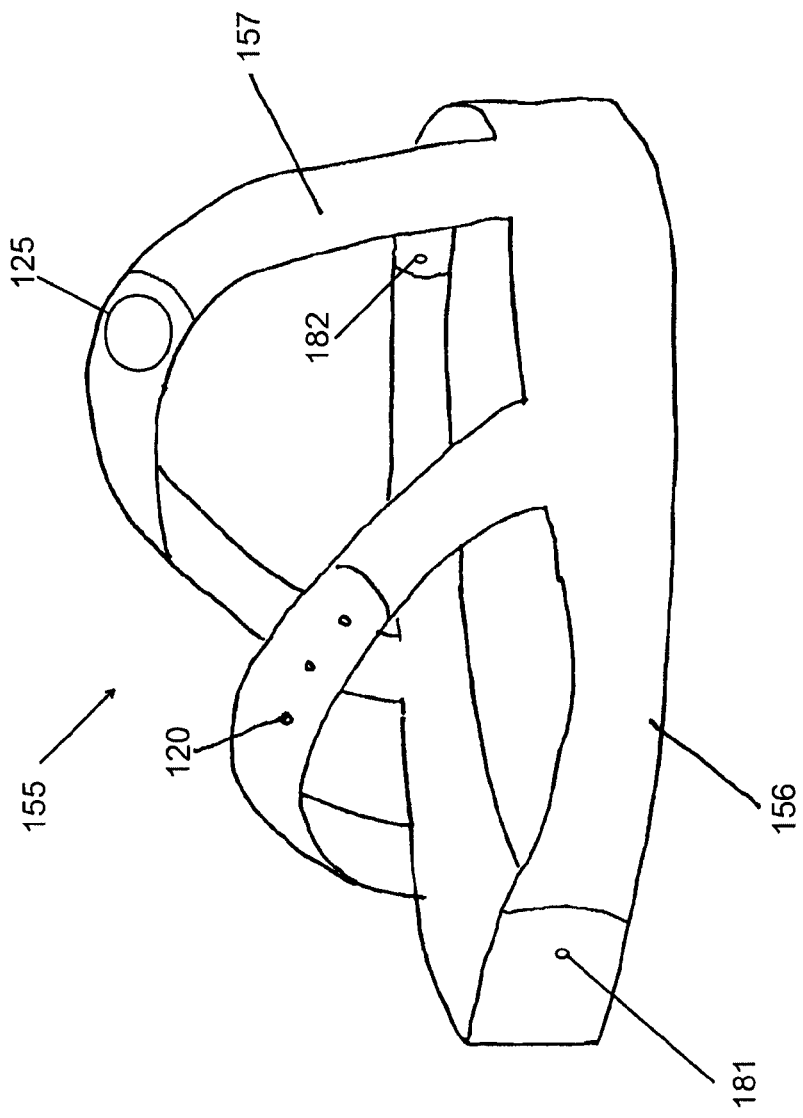
FIG. 2 is an example of one embodiment of headset for use with a surgical headlamp.

The LEDs 145, 146, 147 may attach, directly or indirectly, to a headset 155. (See also FIG. 2). As shown in FIG. 1, the headset 155 may incorporate one or more ratchets 125 to allow for adjustments so the apparatus may accommodate multiple users. The ratchets 125 may be located on the horizontal band 156 and a vertical band 157. Separate bands may be used whereby, through use of various holes 120 and probes, the headset 155 may be customized further. The headset 155 may be composed of semi-ridged plastic. The headset 155 may be constructed so that it is rigid enough to uphold the weight of the LEDs 145, 146, 147 and heat sinks 150, 151 and 152. In addition, the headset 155 may comprise hinges or pivots 181, 182 located on the horizontal band 156, thereby allowing the headlight 130 to collapse into a compact form provided, for example, the vertical bands 157 can be unattached from the headset 155. In other embodiments, instead of attaching to a headset 155, the LEDs 145, 146, 147 are mounted on a belt worn around the user's waist or on a belt fastened to the user's arm.

Furthermore, each LED 145, 146, 147 may be connected to a collimator 140, 141, 142 that directs light from the LED 145, 146, 147 into a fiber optic cable 105, 110, 115. The fiber optic cables 105, 110, 115 guide light from each LED 145, 146, 147 towards a LED combiner 100. The fiber optic cables 105, 110, 115 may extend, independently, from the LEDs 145, 146, 147 to the LED combiner 100. However, they may also be bundled together, in a shielded shroud, to further protect the fiber optic cables 105, 110, 115.

In one embodiment of the invention, a collimator 140, 141, 142 may be avoided by directly connecting the LED 145, 146, 147 to the fiber optic cable 105, 110, 115. In other embodiments, however, a collimator 140, 141, 142, such as the LXHL-NX05 Luxeon Collimator, may be used. (Lumileds Lighting, LLC, 370 West Trimble Road, San Jose, Calif., 95131). Collimators with, for example, 90% efficiency may allow for the use of fewer LEDs to obtain the desired level of brightness. As understood by a person or ordinary skill in the art, items such as glass dowels may be used instead of or in addition to a collimator 140, 141, 142.

In the LED combiner 100, the light from each LED 145, 146, 147 is directed so that each LED's light is combined with light from the other LEDs. The light from each LED 145, 146, 147 may be combined at the LED combiner 100 or projected on a path such that the light from each LED 145, 146, 147 is combined at a focal point that is, for example, twenty-four inches away from the headlight 130. The LED combiner 100 may comprise or be coupled to a fiber optic cable coupler, such as, for example, the 3 to 1 coupler from FOCI Fiber Optic Communications, Inc (20550 Nordhoff St., Chatsworth, Calif. 91311 USA). In one embodiment, the LED combiner 100 may utilize a RGB scrambler 101 to combine the red, green and blue light into, for example, white light. As those or ordinary skill in the art will appreciate, an RGB scrambler 101 or combiner 100, comprised of, for example, multi-gradient lenses may be used. The LED combiner 100 may further comprise a lens 180 and an actuator 175 for actuating the lens. As a result, the light from the LEDs 145, 146, 147 may be focused at various focal points. For example, the light may be focused at 18 inches, 30 inches, or at any point therebetween, to accommodate a user's preferences. The LED combiner 100 may be supported using brackets 160 and/or a telescoping mount. Furthermore, the lens 180 may also cooperate with a pivot joint to allow the user to direct the light beam.

Figure 3:
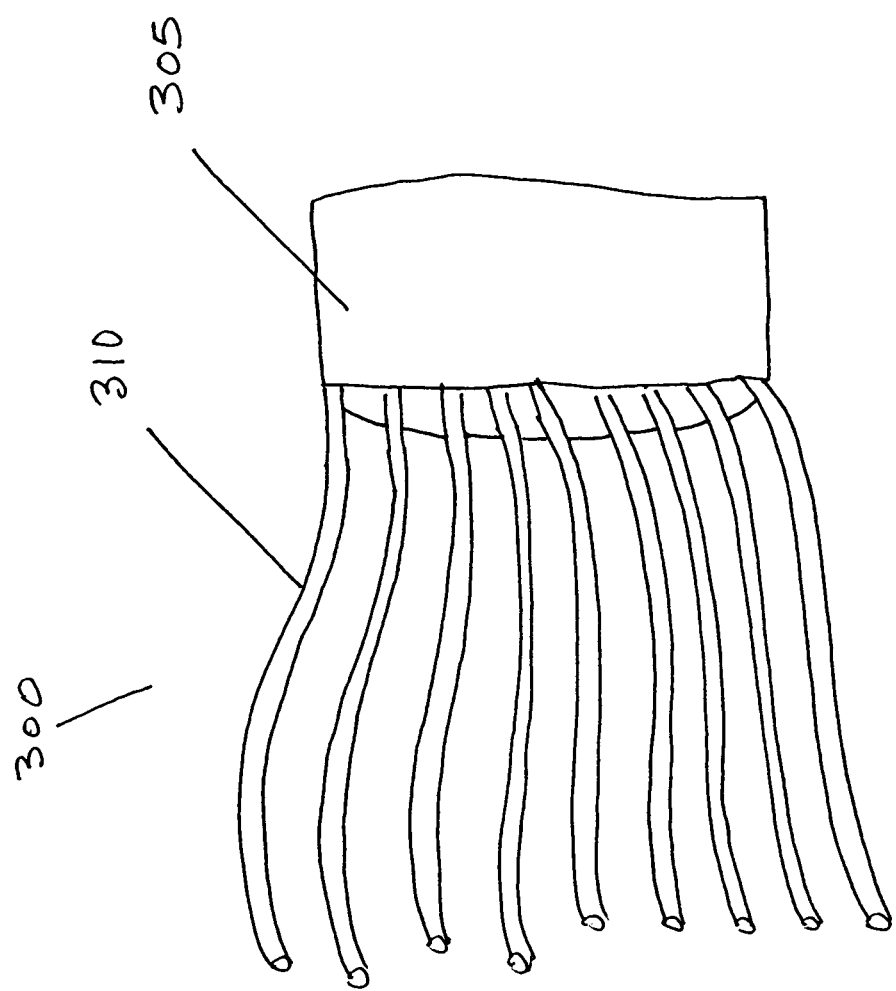
FIG. 3 is an example of one embodiment of a LED combiner.

As shown in FIG. 3, The LED combiner 300 may be constructed by molding, fiber splitting or by gluing glass/quartz single fibers to a base 305 that comprises a lens. Acrylic, polycarbonate, high clarity plastic or any other molded material with low light resistance may be used in constructing the LED combiner 300. Flexible glass or quartz fiber reinforced with a thin coating, for protection, may also be used. A transparent adhesive may be used to couple the fiber optic cable 310 to the LED combiner base 305. The base 305 could be manufactured as a separate piece from the cables 310.

Multiple glass fibers could be used with the headlamp 130. For example, a fiber bundle (e.g., 5,000 to 10,000 fibers) could be split and run to each individual collimator 140, 141, 142.

Those of ordinary skill in the art will appreciate that a laser may substitute for the LEDs 145, 146, 147. For example, white lasers may be so utilized. The LEDs 145, 146, 147 may be coupled to a fiber optic cable 105, 110, 115. However, the laser may be affixed to, for example, the headlight 130 and project light onto the surgical field without use of any fiber optic cable.

One embodiment of the invention weighs less than about 12 ounces.

In still another embodiment, the invention is used to illuminate a surgical scope involved in endoscopic procedures such as, for example, laparoscopic gall bladder removal. The headlight 130 is also appropriate for other lighting environments including: dental, emergency room, paramedics, auto mechanics and mineral mining.

The presently disclosed embodiments are to be considered in all respects as illustrative and not restrictive. The scope of the invention is indicated by the appended claims, rather than the foregoing description, and all changes which come within the meaning and range of equivalency of the claims are, therefore, intended to be embraced therein.

What is claimed is:

1. A surgical headlight for illuminating a surgical field, comprising:
    a surgical headpiece selectively supported by the head of a user;
    at least two light sources supported by and attached to the headpiece and selectively actuated to emit light;
    at least one heat sink in thermal communication with at least one of the two light sources to receive thermal energy from the at least one of the two light sources and dissipate at least a portion of the thermal energy received;
    a combiner including a scrambler in optical communication with the at least two light sources to receive at least a portion of the light emitted from each of the light sources and output substantially-uniform combined light with substantially-uniform intensity and color distribution; and,
    a lens receiving the substantially-uniform combined light and projecting the substantially-uniform combined light into the surgical field.

2. The surgical headlight of claim 1, wherein the light sources combine to provide illumination greater than about 300 lumens.

3. The surgical headlight of claim 2, wherein the light sources combine to provide illumination greater than about 500 lumens.

4. The surgical headlight of claim 1, wherein the light sources comprise three or more LEDs.

5. The surgical headlight of claim 1, wherein the light sources comprise six or more LEDs.

6. The surgical headlight of claim 1, wherein the light sources comprise nine or more LEDs.

7. The surgical headlight of claim 6, wherein the light sources comprise twelve or more LEDs.

8. The surgical headlight of claim 1, wherein the light sources comprise a blue LED, a red LED, and a green LED.

9. The surgical headlight of claim 8, wherein the combiner including the scrambler receives light from the blue LED, light from the red LED, and light from the green LED and outputs substantially-uniform combined light having a white color.

10. The surgical headlight of claim 1, wherein the headpiece comprises a head unit having a front portion, a top portion, a first side portion, a second side portion, and a rear portion, wherein the head unit supports the weight of the light sources and heat sink.

11. The surgical headlight of claim 10, wherein one of the light sources is located on the top portion, another one of the light sources is located on the first side portion, and another one of the light sources is located on the second side portion.

12. The surgical headlight of claim 10, wherein one of the light sources is located on the rear portion, another one of the light sources is located on the first side portion, and another one of the light sources is located on the second side portion.

13. The surgical headlight of claim 10, further comprising a power supply mounted apart from the user's head.

14. The surgical headlight of claim 10, wherein the heat sink is remotely located from the projection lens.

15. The surgical headlight of claim 1, further comprising:
    an actuator coupled to the lens to selectively provide multiple focal points for the substantially-uniform combined light.

16. The surgical headlight of claim 1, further comprising a current-balancing circuitry coupled to two or more of the light sources, wherein the current-balancing circuitry is configured to selectively permit projection of substantially-uniform combined light having a specific color temperature different from the color temperature of at least one of the light sources.

17. The surgical headlight of claim 1, wherein said light source includes a blue LED, a red LED, and a green LED, wherein said combiner extracts light from said blue LED, light from said red LED, and light from said green LED to produce a pre-determined color temperature.

18. A surgical-illumination system comprising:
    at least two light sources selectively actuated to emit light;

a combiner including a scrambler in optical communication with the at least two light sources to receive at least a portion of the light emitted from the at least two light sources and output substantially-uniform combined light with substantially-uniform intensity and color distribution;

a surgical headpiece adapted for wearing on a person's head and having a front portion and a rear portion, the at least two light sources attached to the surgical headpiece;

a head lens supported by the front portion of the surgical headpiece and receiving the substantially-uniform combined light and projecting the substantially-uniform combined light onto an area; and, wherein the light sources are combined by the combiner to provide an illumination of at least 300 lumens.

19. The system of claim 18, wherein the at least two light sources are located on the rear portion of the surgical headpiece.

20. The system of claim 19, further comprising:
a heat sink supported by the rear portion of the surgical headpiece and in thermal communication with one or more of the light sources.

21. The system of claim 18, wherein the at least two light sources include a blue LED, a red LED, and a green LED, wherein said combiner including the scrambler receives light from the blue LED, light from the red LED, and light from the green LED and outputs substantially-uniform combined light having a white color.

22. The system of claim 18, further comprising a collimator coupled to each of the at least two light sources, the collimator directing light from the light sources into the combiner.

23. The system of claim 18, further comprising a power source coupled to at least one of the light sources.

24. A method for providing illumination with a surgical headlight having a headpiece, the method comprising:
providing at least two light sources selectively emitting light, the at least two light sources supported by a user at a location remote from the user's eyes,
combining and scrambling light from at least two light sources to provide combined light with substantially-uniform light intensity and color distribution; and,
receiving and focusing the substantially-uniform combined light at a lens to project the substantially-uniform combined light onto a working area;
wherein the lens is disposed on a front portion of the headpiece, and wherein the light sources are disposed on a user's body and spaced from the front portion of the headpiece.

25. The method of claim 24, wherein the at least two light sources emit light sufficient for the lens to provide illumination greater than about 300 lumens.

26. The method of claim 24, wherein the at least two light sources emit light sufficient for the lens to provide illumination greater than about 500 lumens.

27. The method of claim 24, wherein the step of receiving and focusing the substantially-uniform combined light includes actuating the lens to selectively provide multiple focal points for the substantially-uniform combined light.

28. The method of claim 24, wherein the at least two light sources include at least a blue LED, a red LED, and a green LED.

29. The method of claim 24, wherein at least one of the light sources is disposed on a rear portion of the headpiece and wherein the method further comprises the step of:
directing heat generated by the at least one of the light sources away from the user.

30. The method of claim 24, further comprising the steps of:
transferring thermal energy from at least one of the light sources to a heat sink in thermal communication with the at least one of the light sources, the heat sink disposed between the at least one light source and the user's skin; and
dissipating thermal energy from the heat sink to surrounding air.

* * * * *